United States Patent [19]
Young et al.

[11] Patent Number: 5,847,292
[45] Date of Patent: Dec. 8, 1998

[54] SHEET FLOW WATER QUALITY MONITORING DEVICE

[75] Inventors: George Kenneth Young; Frank R. Graziano; Stuart M. Stein, all of Springfield, Va.

[73] Assignee: GKY & Associates, Inc., Springfield, Va.

[21] Appl. No.: 839,397

[22] Filed: Apr. 11, 1997

Related U.S. Application Data

[60] Provisional application No. 60/040,018 Mar. 4, 1997.
[51] Int. Cl.$^6$ ...................................................... G01N 1/12
[52] U.S. Cl. .......................................................... 73/864.63
[58] Field of Search ........................... 73/863.52, 864.51, 73/864.73, 864.81, 864.91, 864.63; 210/164

[56] References Cited

U.S. PATENT DOCUMENTS

| | | | |
|---|---|---|---|
| 2,119,923 | 6/1938 | McIntyre | 210/164 |
| 3,127,821 | 4/1964 | Le Baron | 210/164 |
| 4,454,039 | 6/1984 | McCoy | 210/164 |
| 4,958,528 | 9/1990 | Garrison | 73/864.63 |
| 5,186,052 | 2/1993 | Gray | 73/215 |
| 5,413,005 | 5/1995 | Gray | 73/863.52 |
| 5,524,495 | 6/1996 | Dudley | 73/864.63 |

*Primary Examiner*—Richard Chilcot
*Assistant Examiner*—Jewel V. Thompson
*Attorney, Agent, or Firm*—Jim Zegeer, Esq.

[57] ABSTRACT

A runoff water monitoring system for sampling sheet-flow from a generally flat surface having an edge comprises an elongated recess contiguous to the edge and depending below the generally flat surface. An insert in the recess has an upper end and an open frame plate member. A grate member is secured to the open frame and has a downwardly depending sample receptacle attachment sleeve and a grate plate having a predetermined number of sheet-flow metering apertures therein. A sample collection receptacle is releasably secured on the attachment sleeve to receive water flowing through the sheet-flow metering apertures. The sheet-flow metering apertures are preferably rectangular and have a rounded leading or upstream edge and square side and back edges. The sample receptacle over the attachment sleeve which has an endless groove in the sleeve and an endless elastic member is seated in the groove over the open end of the sample receptacle. The sample receptacle attachment sleeve includes an internal baffle for trapping floating pollutants. The sample receptacle has an indicia space to write collection data and a tongue-and-groove type seal spaced a predetermined distance below the mouth of the sample receptacle.

24 Claims, 7 Drawing Sheets

SHEET FLOW WATER QUALITY MONITORING DEVICE

The present application is the subject of provisional application Ser. No. 60/040,018 filed Mar. 4, 1997 and entitled SHEET-FLOW WATER QUALITY MONITORING DEVICE and incorporated herein by reference.

BACKGROUND

1. Field of the Invention

This invention relates to a surface water quality monitoring device and method specifically designed to capture sheet-flow samples in flush-shouldered highway environments, parking lots, roofs, and other flat or substantially flat surfaces upon which rain falls and runs off.

2. Description of Prior Art

This invention was developed in response to a solicitation from the federal government, specifically from the U.S. Department of Transportation, Small Business Innovation Research (SBIR) Program, Solicitation No. 96-1. In the solicitation, the need for such a device is stated as follows:

"Monitoring the water quality of stormwater runoff is becoming an often stipulated requirement in permits and other authorizations needed by transportation agencies to construct, maintain and operate highway facilities. Traditional monitoring equipment requires channelized, piped or otherwise collected flow volumes in order to operate properly and provide accurate results. However, many highway sites do not drain stormwater through collection systems. Often, drainage occurs by sheet-flow over flush shoulders to the side slopes. The use of traditional water quality monitoring equipment on these sites may require extensive drainage modifications to collect storm flows, often at significant expense. Certain sheet-flow samplers are commercially available, however, their successful application to highway flush-shoulder conditions has not been encouraging. A simple and inexpensive sampling device is needed that can collect sheet-flows from flush-shouldered highway sections to produce accurate discrete or composite water samples during a storm event."

As stated in the solicitation, other sheet-flow samplers are available. One such sampler, developed by the California Department of Transportation (CALTRANS), is known as the splitter flume. It consists of a plywood ramp onto which thin, metal vanes are attached. The vanes are bent and calibrated such that flow progressing down the ramp is progressively split, such that a water sample is reduced to 1% of the total volume entering the device and is isolated for capture and analysis. This device has recognized limitations:

(a) It's large, roughly the size of a sheet of plywood, making it noticeable to passers-by. Large, noticeable monitoring devices are often subjected to vandalism.

(b) It has to be made and hydraulically calibrated at some expense.

(c) It's not passive; it cannot be installed and left to capture the runoff volume unattended.

(d) It cannot be installed anywhere. It requires a concentrated collection point, such as a gap in a curb.

Another device for capturing runoff is known as the Coshocton wheel. It operates with a rotating wheel that "slices" off a representative water volume. It has many of the limitations of the splitter flume listed above. In addition, it requires head to operate (head is basically the pressure produced by a column of fluid, in this case, water). As a result, runoff must be captured and stored until it builds up to a sufficient depth to "drive" the device.

A third device is known as the Vortox Liquid Sampler (patent pending) developed by the Vortox Company. It consists of a circular, stainless steel receptacle placed below a grate. On top of the receptacle is an orifice through which the water sample is captured. The rate at which water is captured is set by a float and ball valve assembly that also seals the unit when full. The valve is adjusted to set the desired time rate of capture, at increments of about 0.02 gpm. The Vortox Liquid Sampler is designed to be suspended in manholes or pipes or can be installed in the ground to capture surface runoff.

While the Vortox Liquid Sampler is believed the closest device to the present invention, there are several significant differences that make the sheet-flow water quality monitoring device disclosed herein superior and uniquely designed to accurately capture sheet-flow runoff from pavement surfaces:

(a) The Vortox Liquid Sampler captures flow through an orifice, not a weir as does this invention. As a result, the entire depth of flow from the water column is not sampled. This invention guarantees a representative sample.

(b) The rate of capture of the Vortox Liquid Sampler is set based on time. Given the variable nature of rain events, it would be impossible to calibrate the Sampler to capture sheet-flow at the same rate it is running off the pavement. This invention, however, captures all sheet-flow hitting the sample ports, regardless of the intensity of the rain event and yields a representative sample. The Vortox Liquid Sampler, therefore, would not capture a sample as directly representative of the sheet-flow from the entire road surface as would our invention.

(c) Since the Vortox Liquid Sampler captures flow based on a time rate, it cannot be set to capture a desired runoff volume, such as the first 13 mm. Given a constant flow rate, which does not occur in rain events, it can be calibrated to fill up in a set amount of time, say 30 minutes. This invention, however, can be very easily configured to capture a representative volume from the entire road surface that is independent of time and depth of flow.

(d) While the Vortox Liquid Sampler is fairly simple to operate, it is more complicated than our invention. This invention requires no calibration, has no moving parts, and is not oriented to a time rate of capture.

(e) The Vortox Liquid Sampler is not specifically designed to capture sheet-flow runoff from highway sections.

(f) The Vortox Liquid Sampler is more difficult to fabricate.

OBJECTS AND ADVANTAGES

The objects and advantages of this invention include the following:

(a) to provide a sheet-flow sampler that is small, inexpensive, and expendable;

(b) to provide a sheet-flow sampler that can be easily configured to capture different runoff volumes that are representative of the entire roadway section;

(c) to provide a sheet-flow sampler that accurately captures the desired runoff volume, regardless of the depth of the sheet-flow (within the range of expected rainfall totals);

(d) to provide a sheet-flow sampler that is unobtrusive and entirely passive;

(e) to provide a sheet-flow sampler that is resistant to roadside trauma;

(f) to provide a sheet-flow sampler that requires no special skills to install and maintain;

(g) to provide a sheet-flow sampler that traps floating pollutants with an internal baffle;

(h) to provide a sheet-flow sampler that contains within itself the storage container for the collected sample; and (i) to provide a sheet-flow sampler that can be installed in a variety of highway environments.

DESCRIPTION OF THE DRAWINGS

The above and other objects, advantages and features of the invention will become more clear when considered with the following specification and accompanying drawings, wherein.

Figure 1:
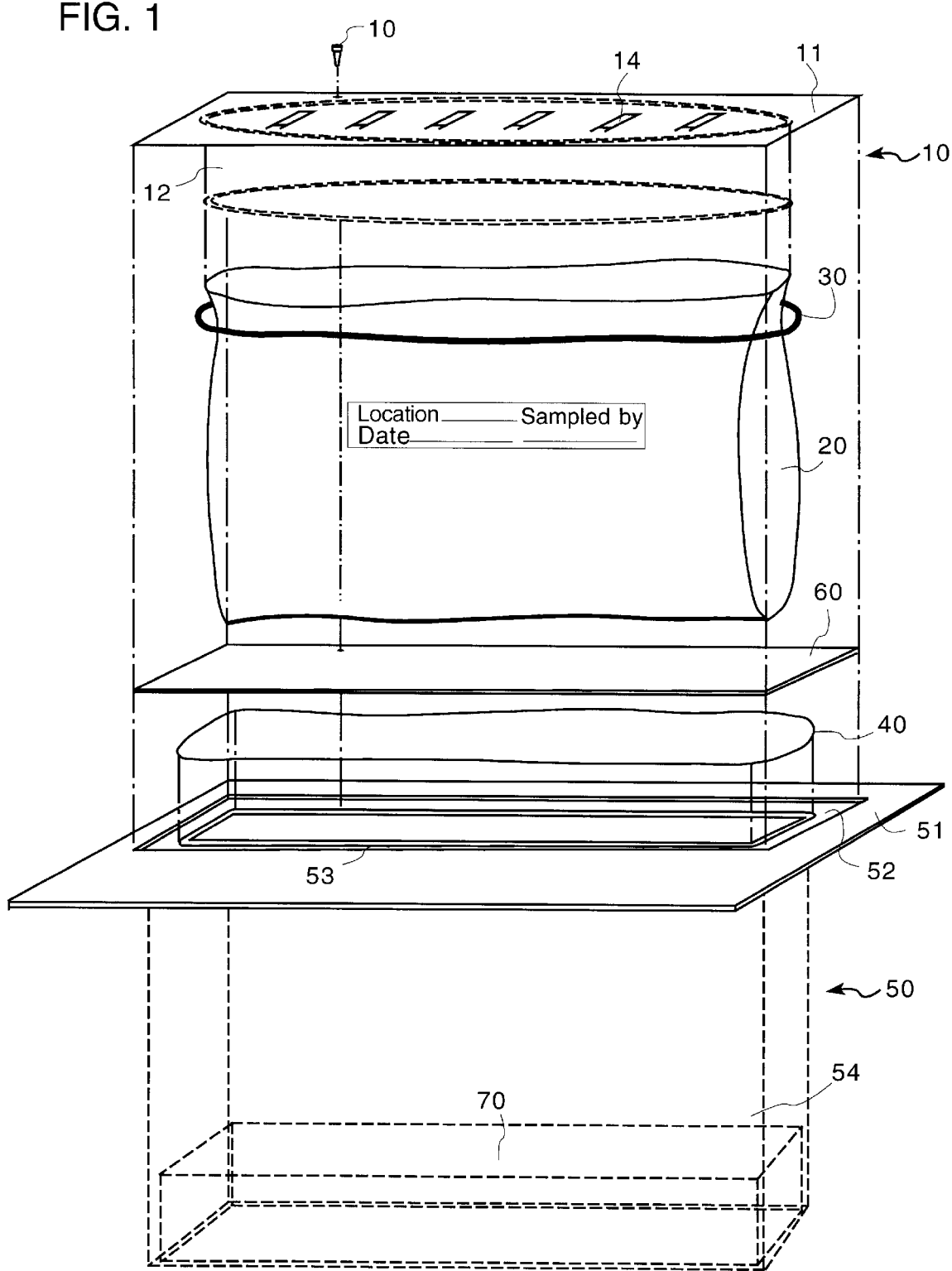
FIG. 1 shows an exploded view of a preferred embodiment of the entire sampling device, including a grate, a sample receptacle, a protective plate, an insert, two o-rings.

REFERENCE NUMERALS IN DRAWINGS 10 grate
11 grate top
12 grate sleeve
13 internal baffle
14 sample-ports
15 sample-port leading edge
16 sample-port side and back edges
17 o-ring gland
18 machine screws
20 sample receptacle
30 o-ring
40 o-ring
50 insert
51 insert top
52 insert recess
53 o-ring gland
54 insert body
60 protective plate
70 spacer

SUMMARY

The sheet-flow water quality monitoring device is comprised of three basic parts; a grate, an insert, and a collection receptacle.

DETAILED DESCRIPTION OF THE INVENTION

Figure 2:
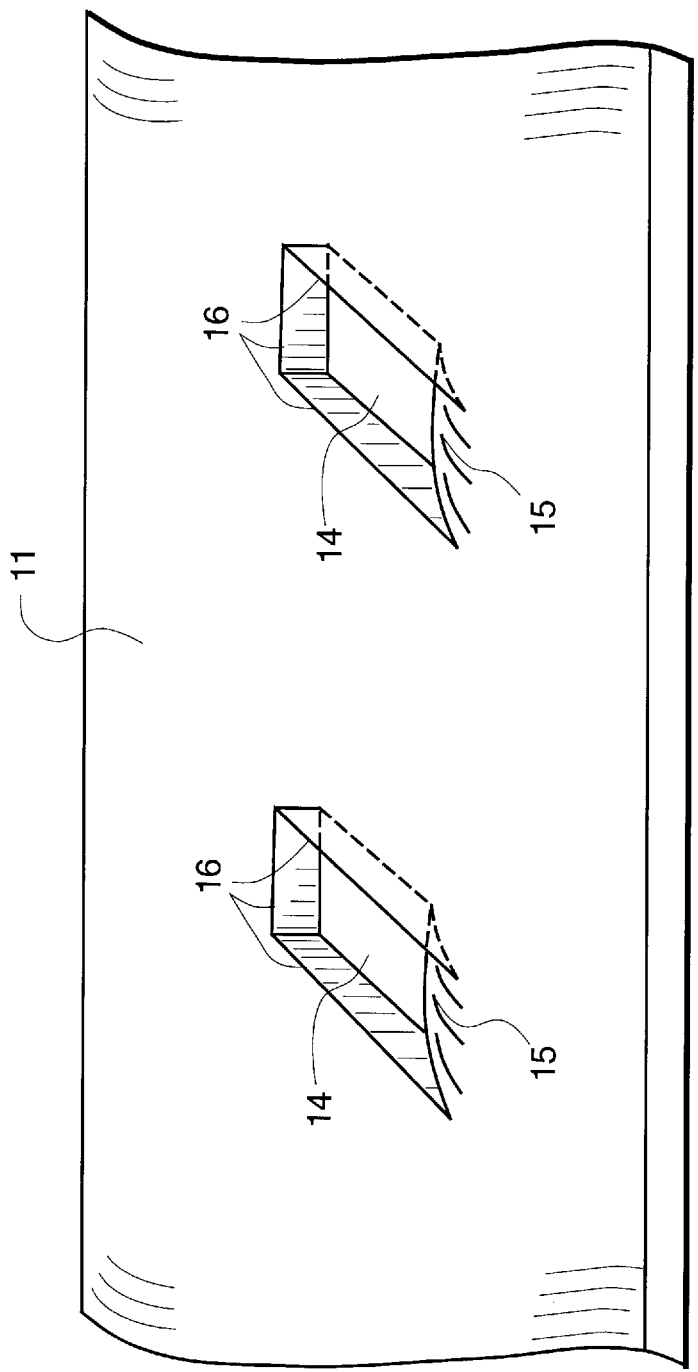
FIG. 2 shows a close-up of the grate surface, emphasizing the 3 square and 1 rounded edge of the samples-ports.
Figure 3:
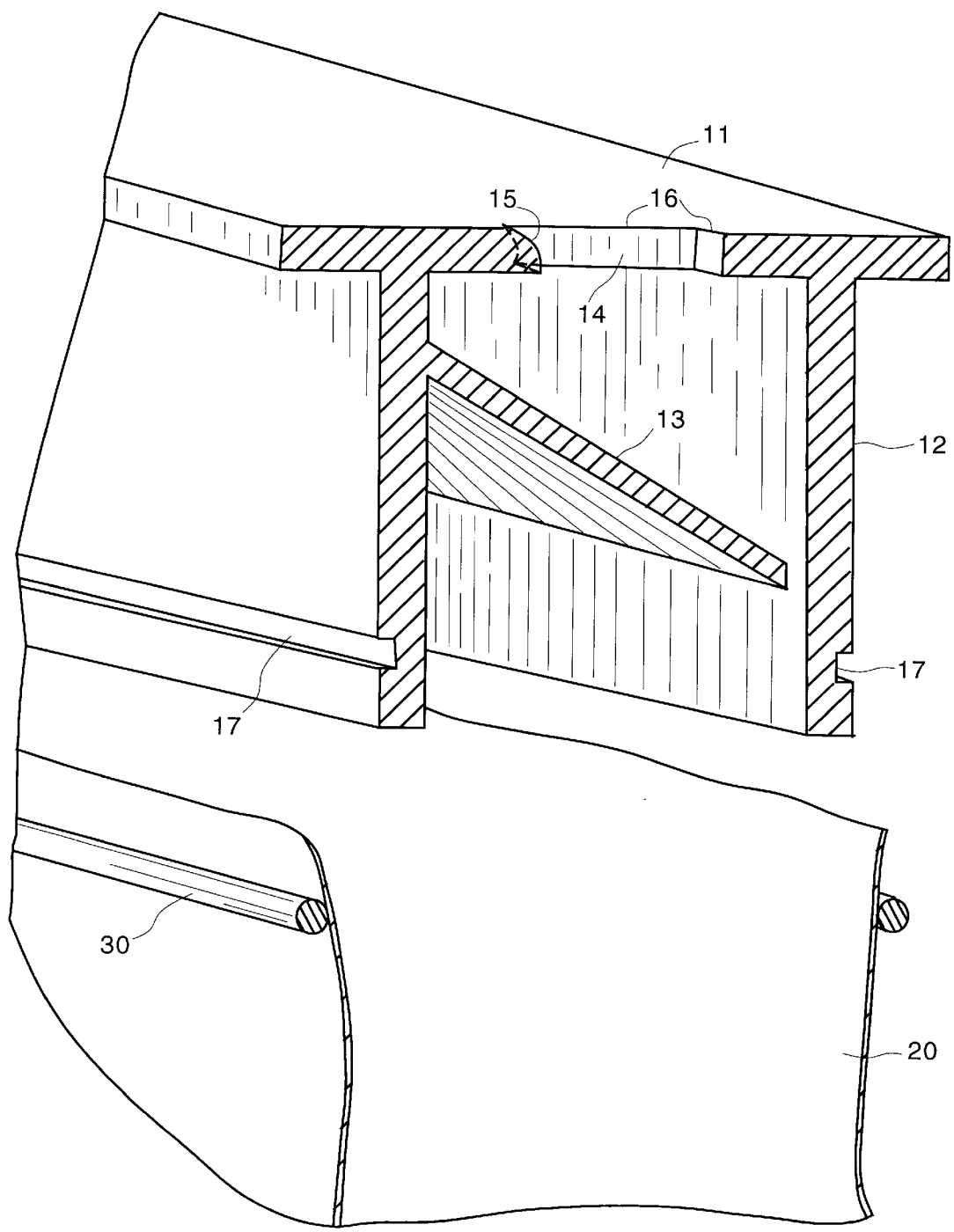
FIG. 3 shows a cross-section of the grate through a typical sample-port. The orientation of an internal baffle displayed, along with sample-port edge configurations a sample receptacle means of attachment.

Referring now to FIGS. 1–3, FIG. 1 shows a typical embodiment of the sheet-flow water quality monitoring device incorporating the invention. The device consists of a grate 10, a sample receptacle 20, o-rings 30 and 40, an insert 50, and a protective plate 60. The FIG. 1 exploded view further shows how the main components combine to form the entire sheet-flow water quality monitoring device. The sample receptacle 20 attaches to the grate section 10 on a grate sleeve 12. The sample receptacle 20 is held in place on the grate sleeve 12 with the o-ring 30. The o-ring 30 is seated in an o-ring gland or groove 17, shown in FIG. 2, such that the walls of the sample receptacle 20 are sandwiched between the o-ring 30 and the grate sleeve 12, holding sample receptacle 20 in place. The grate sleeve 12 with the attached sample receptacle 20 fits inside the insert 50. A grate top 11 fits inside an insert recess 52, located in an insert top 51, such that the grate top 11 is flush with the insert top 51. An o-ring 40 fits inside an o-ring gland or groove 53 located in the insert recess 52. Machine screws 18 are used to attach the grate 10 to the insert 50, lightly compressing the o-ring 40, providing a seal. The machine screws 18 also provide a means for making the grate top 11 flush with the insert top 51. A spacer 70 can be placed in the insert body 54 to limit the sample volume. This will be discussed in more detail in a following section. When not configured to actively collect a sample, a protective plate 60 is installed in the insert recess 52 to keep water and debris out of the insert body 54.

The grate section 10, in the preferred embodiment, is made of a chemically inert plastic, such as high-density polyethylene (HDPE) or Teflon® fluorinated ethylene propylene (abbreviated as FEP). The grate 10 is manufactured as one piece using plastic injection mold techniques. The grate top 11, the grate sleeve 12, and the internal baffle 13 have a nominal 3 to 4 mm thickness. The overall size of the grate top 11 is a nominal 495 mm long by 91 mm wide. In this embodiment, the grate sleeve 12 is oval in shape (it could also be rectangular), a nominal 465 mm long by 65 mm wide by 60 mm deep.

The sample receptacle 20 is made of chemically inert plastic, such as HDPE, and has a nominal thickness of about 2 mil. The size of the sample receptacle 20 can vary, but should be long enough to allow the grate 10 to be lifted roughly 15 cm from the insert 50 while the top of the sample receptacle 20 is attached to the grate sleeve 12 and the bottom of the sample receptacle 20 is resting on the bottom of the insert body 54. Preferably, the sample receptacle 20 should also have a zip-lock or other seal located roughly 50 mm from the top edge. In addition, sample receptacle 20 preferably has an indicia or label area for entering such data as "location" of the sampling site, "date", etc.

The o-rings 30 and 40 are made of an elastomer, such as Buna-N, and are available from Apple Rubber Products of Lancaster, N.Y.

The insert 50 is preferably one piece and is manufactured of a chemically inert metal, such as stainless steel. The insert top 51 and the insert body have nominal thickness of 6 to 7 mm. The overall, nominal size of the insert top 51 is 520 mm long by 195 mm wide and the insert body is nominally 490 mm long by 80 mm wide by 320 mm deep.

The protective plate 60 is made from a rust resistant metal, such as aluminum, and has a nominal size of 495 mm long by 90 mm wide. The thickness of the protective plate 60 is a nominal 3 to 4 mm.

The spacer 70 can be made of any material as it does not contact the water sample; with cost in mind, plastic is preferred. The spacer 70 fits easily within the insert body 54, with the height dependent on the application and volume of sample to be collected.

The grate section 10 is shown in FIG. 1 with six sampling ports 14. This is a typical embodiment, but will vary depending on the desired representative runoff volume and runoff length. These parameters will be discussed in greater detail in the following section. The configuration of the sample-port(s) 14 is shown in greater detail in FIG. 2. The sample-port(s) 14 are rectangular in shape with a typical dimension of 6.5 mm wide by 25.5 mm long, with the long axis of the sample-port(s) 14 perpendicular to the long axis of the grate section 10. A sample-port leading edge 15 of the sample-port(s) 14 is sloped or rounded with a typical radius of 13 mm. The sample-port(s) 14 run through grate top 11. The sample-port(s) 14 has three remaining edges, sample-port side and back edges 16. The sample-port side and back edges 16 are square.

FIG. 3 depicts a cross-section of the grate section 10. The internal baffle 13 is molded into the grate sleeve 12 along three sides, one long side and both short sides. The internal baffle 13 is angled downward toward, but does not touch, the long, back side of the grate sleeve 12. A gap of about 7 mm exists between the downward edge of the internal baffle 13 and the back side of the grate sleeve 12. Also shown in FIG. 3 is a cross-section through a typical sample-port(s) 14 showing the rounded sample-port leading edge 15 and the square sample-port side and back edges 16.

These materials and dimensions are intended to be exemplary of a preferred embodiment.

From the description above, a number advantages of our sheet-flow water quality monitoring device over the prior art become evident and include one or more of the following:

(a) the device is small, unobtrusive, and very simple to install and maintain;

(b) plastic injection manufacturing will enable the grate section to be mass produced, keeping costs low;

(c) the preferred embodiment of the sample-port edges (rounded leading edge and square side and back edges) provide a capture efficiency that is independent of runoff depth within practical ranges;

(d) the preferred embodiment incorporating the sample-port leading edge will advantageously capture very low sheet-flow depths and out-perform other edge configurations;

(e) the orientation of the device normal (perpendicular) to the sheet-flow can be ±10° from normal without significantly influencing performance;

(f) the modular design of the water quality monitoring device allows for a permanent sampling location to be used repeatedly at low cost;

(g) the grate and sample receptacle can be installed in a matter of minutes into the permanently installed insert;

(h) the ease of installation and low cost will combine to dramatically increase the quantity and quality of water quality data from highway runoff;

(i) and the use of a flexible, plastic sample receptacle will keep costs low and provide maximum flexibility in capturing desired runoff volumes that are representative of the entire roadway section.

OPERATION-FIGS. 1 to 5

Installation

Figure 4:
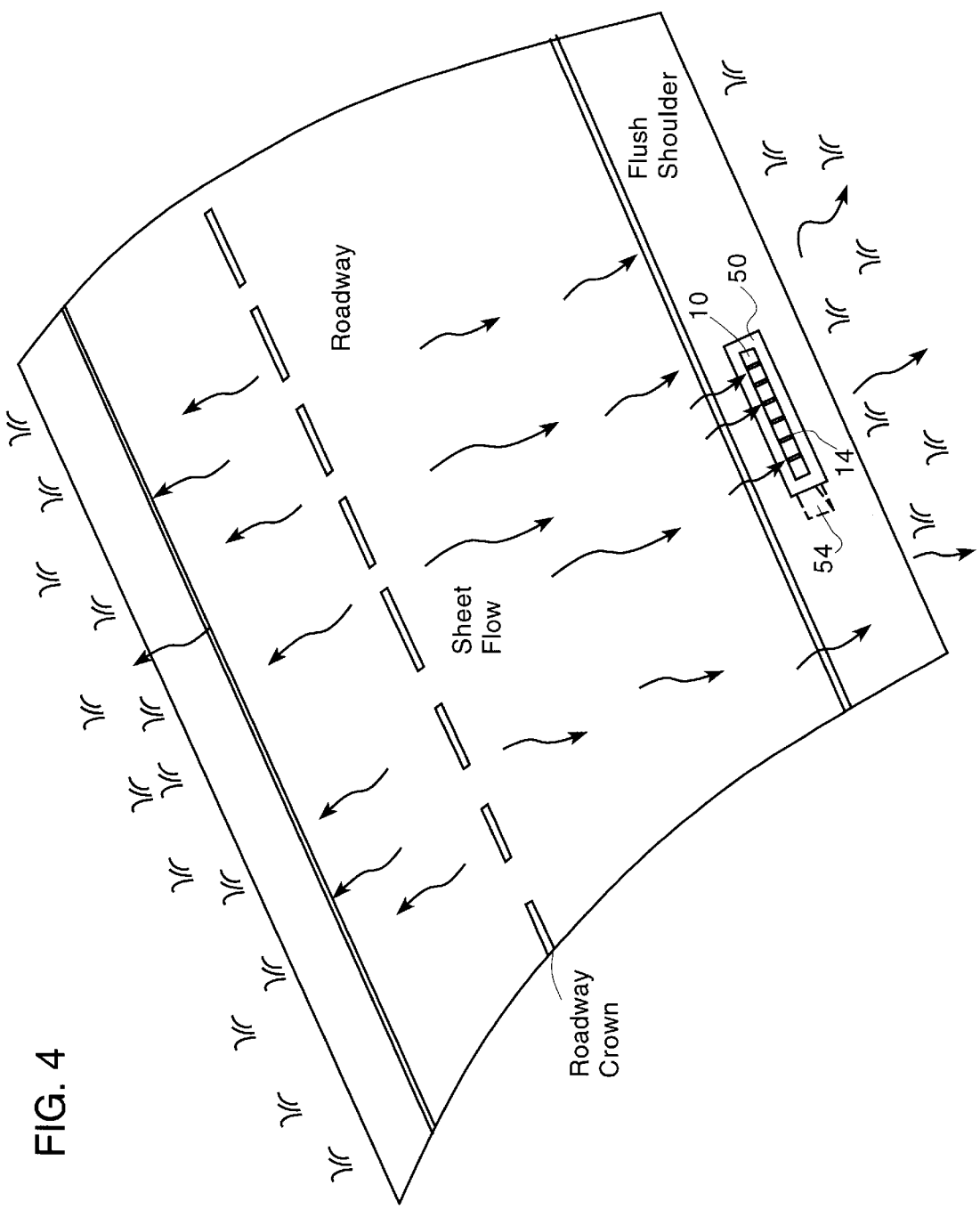
FIG. 4 shows an application of the sheet-flow sampler along a typical, flush-shouldered roadway section.
Figure 5:
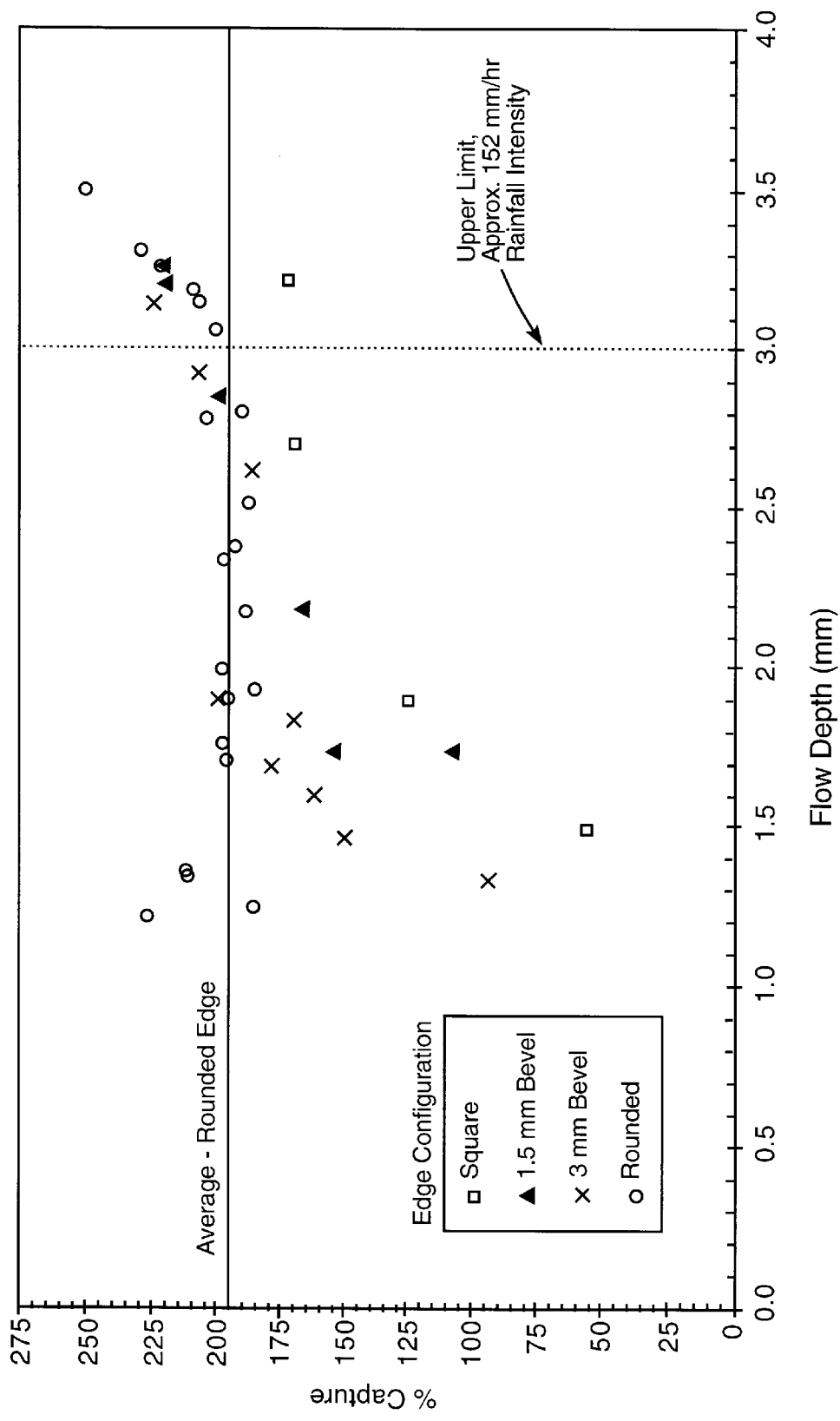
FIG. 5 shows the results of tests on different sample-port leading edge configurations using an acrylic model.

The sheet-flow water quality monitoring device disclosed herein is designed to capture sheet-flow off of highway sections. Sheet-flow can be described as the thin film of water that runs off of surfaces during rain events. The depth of sheet-flow ranges up to about 3 mm for the most intense rain events. The primary application, depicted in FIG. 4, is in highway environments with flush shoulders such that runoff from the roadway spreads out on the adjacent ground surface prior to entering any roadside conveyance, such as a ditch or channel. Our sheet-flow water quality monitoring device can, however, be applied in any highway environment in which there is sufficient shoulder area in which the runoff remains as sheet-flow.

As shown in FIG. 4, the sheet-flow water quality monitoring device is installed with the long axis of the device, perpendicular to the direction of the sheet-flow runoff. The sample-port(s) 14, shown in FIGS. 1 to 4, are aligned parallel to the direction of sheet-flow, with the sample-port leading edge 15 oriented upstream such that sheet-flow enters the sample-port(s) 14 through the sample-port leading edge 15.

The insert 50, shown in FIG. 1, is permanently installed in the highway shoulder by placing the insert body 54 below grade such that the insert top 51 is flush with the shoulder surface and the long axis of the insert top 51 is perpendicular to the direction of sheet-flow runoff. The device is supported by the insert top 51 that rests on a ledge cut into the pavement. The hole containing the insert body 54 should be dug just deep enough to contact the bottom of the sampler body 54. The void between the sampler body 54 and the soil should be kept as small as possible, and should be backfilled with any appropriate material to secure the device. The edge between the insert top 51 and the pavement should be sealed with a non-hydrophobic material, such as an epoxy resin, to keep surface water from entering the void around the insert body 54. Once installed, this becomes a permanent sampling location that can be repeatedly, easily, and inexpensively utilized to gather highway runoff water quality data.

Sampling

Prior to the onset of rainfall for which water quality data is desired, the protective plate 60 is removed from the insert top 51. The sample receptacle 20 is secured to the grate sleeve 12 with the o-ring 30. The sample receptacle 20 is lowered into the insert body 54 and the grate is pushed into the insert recess 52. The machine screws 18 are lightly turned until the grate top 11 is flush with the insert top 51.

Some time after the rain event is over, the grate 10 is carefully lifted from the insert 50, leaving the portion of the sample receptacle 20 with the captured water sample resting on the bottom of the insert body 54 or, if so equipped, on the spacer 70. The sample receptacle 20 is then sealed, before removing from the grate sleeve 12, lifted from the insert body 54, and transported to the laboratory for analysis. The protective plate 60 is then re-installed on the insert top 51. After the sample is removed, the grate 10 can either be cleaned for re-use or discarded if damaged.

Theory of Operation

Our sheet-flow water quality monitoring device can be easily configured to capture various runoff volumes over various pavement (or flat surface) runs from the high point to the device. The runoff volume is defined as the depth of runoff over a defined surface area. It is less than the rainfall depth over the same surface area by the amount of storage in the surface texture of the roadway. The first 12.5 mm of runoff is often considered to be the "water quality volume" as it represents the "first flush" of a rain event. The "first flush" typically contains the highest pollutant load as pollutants tend to build-up on the road surface between rain events. Other volumes may be of interest, such as the first 25 mm, etc.

The sample-ports(s) 14 and the use of an over-sized, interchangeable sample receptacle 20 with the spacer 70 were designed with the desire for capturing different sample volumes in mind. The theory of how the sample-port(s) 14 and sample receptacle 20 combine to capture a desired runoff volume is very simple. The size and number of the sample-port(s) 14 and the volume of the sample receptacle 20 can be configured so that the water quality monitoring device is exactly filled by the desired runoff volume. When full, any runoff in excess of the desired runoff volume will overtop the device and will not be captured. The internal baffle 13 traps floating pollutants within the sample body 54, preventing them from rising up and out of the device.

Figure 6:
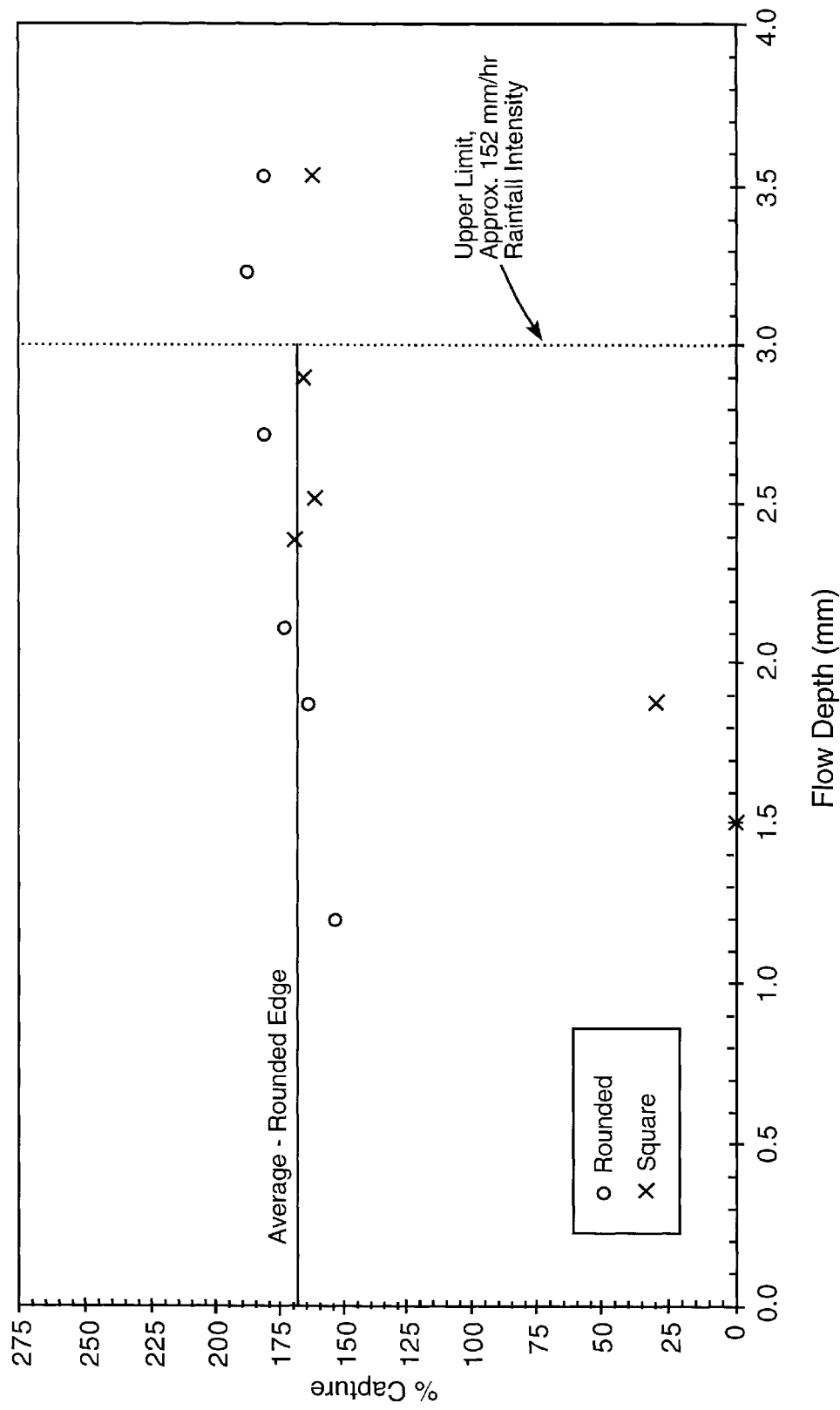
FIG. 6 shows the results of tests on a prototype deice with different sample-port edge configurations.

In order for the above theory to function properly, the sample-port(s) 14 must capture a predictable percentage of the sheet-flow runoff hitting the sample-port leading edge 15. In addition, the percentage of sheet-flow runoff captured by each sample-port(s) 14 must be independent of the sheet-flow runoff depth. This leads to the importance of the design of the sample-port leading edge 15 as well as the sample-port side and back edges 16. Tests were performed on various sample-port leading edge configurations, from a square edge to the gradual rounding depicted in the sample-port leading edge 15 of our device. The results of testing on an acrylic model, shown in FIG. 5, reveal that our rounded sample-port leading edge 15 was the only configuration tested that provided a predictable percent capture over the practical range of runoff depths. This practical range includes important lower runoff depths for which other edge configurations did not as readily accept runoff due to the sharper edges. Thus, most rain events that begin with a low intensity, or those in which the intensity remains low over the entire event, would not be accurately represented when using a sampler with other edge configurations. Similar results, shown in FIG. 6, were achieved on a prototype device manufactured from aluminum.

Figure 7:
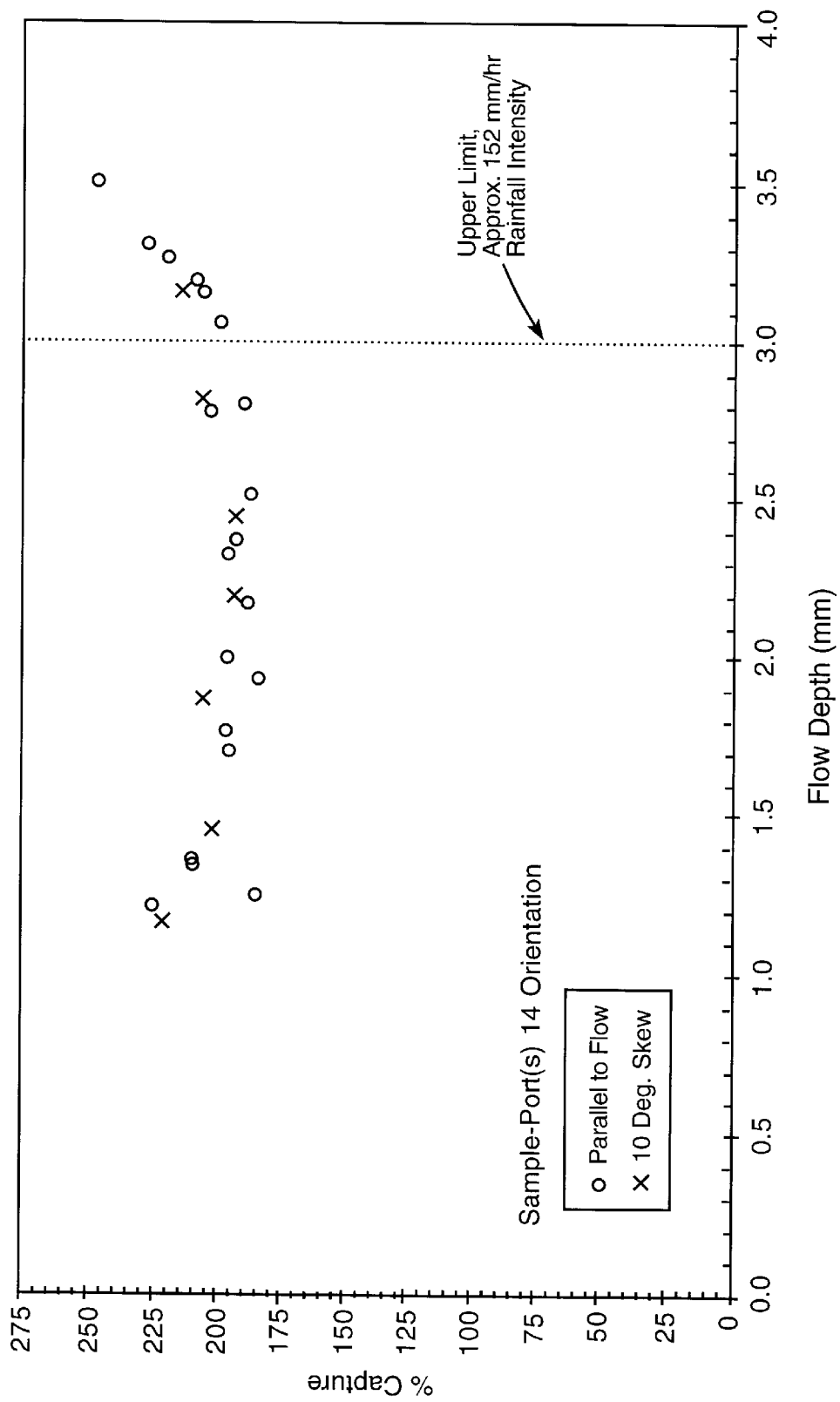
FIG. 7 shows the results of tests to see how improper installation might affect capture efficiency.

The importance of the square sample-port side and back edges 16 can be seen in FIG. 7. For this test, the sample-ports were oriented at a skew of 10 degrees from parallel to test the upper limit of reasonable error that may be encountered in the field. FIG. 7 shows that a skew of at least up to 10 degrees had no effect on the capture percentage of the sample-ports. The square edge is not breached by the sheet-flow, even at a skew of 10 degrees.

Given the predictable nature of the capture efficiency of the sample-port(s) 15, volume of the sample receptacle 20 can be determined using the following equation:

$$V_{sampler} = 0.001 \times D_{Runoff} \times L_{Flow} \times W_{Ports} \times N_{Ports} \times Eff_{Por}$$

Where $V_{Sampler}$=Required volume of sample receptacle 20, L $D_{Runoff}$=Desired runoff capture depth, mm (i.e. first 13 mm)

$L_{Flow}$=Runoff flow length, m $W_{Ports}$=Width of sample-port(s) 14, mm $N_{Ports}$=Number of sample-port(s) 14

$Eff_{Ports}$=Capture efficiency of sample-port(s) 14

0.001=Conversion factor

To illustrate a practical application, assume a sample location is on a roadway that has a drainage length, from the roadway crown to the sampler, as shown in FIG. 4, of 7 m. Further assume it was desirable to capture the first 13 mm of runoff. The sheet-flow sampler at the site is equipped with 6 sample-port(s) 14, each with the preferred width of 6.4 mm. Using the efficiency obtained in the laboratory of 1.68 (168%), the required volume of the sample receptacle 20 would be 5.9 L. If the number of sample-port(s) 14 were reduced to 3, the required volume of the sample receptacle 20 would be half as much, or 2.9 L. Having fewer sample-port(s) 14 has the benefit of a smaller sample volume, but also has a disadvantage should one of the sample-port(s) 14 become blocked; the capture efficiency of the entire device would be reduced by one-third instead of one-sixth.

SUMMARY, RAMIFICATIONS, AND SCOPE

Thus, the sheet-flow water quality monitoring device disclosed herein satisfies the recognized need for a simple to operate, low cost, reliable, and accurate sheet-flow water quality monitoring device. The invention provides the user with maximum flexibility in the number of suitable sampling locations available as well as in capturing the user specified runoff volume. The sheet-flow water quality monitoring device and system of this invention is easily installed and maintained, is entirely passive, and will dramatically increase the quantity and quality of highway runoff water quality data. In addition, the device captures runoff that is representative of the entire roadway section.

While the above description of our invention contains many specificities, these should not be construed as limiting the scope of the invention but as merely providing illustrations of some of the presently preferred embodiments of this invention. Aspects of this invention can be varied. For example, the overall rectangular shape and size of the device can have different dimensions (the narrow dimension was chosen so that a car tire could span the opening, causing no damage); the sample receptacle can be made from a rigid material, manufactured as one piece with the grate or as two separate pieces; the means by which the modular sample receptacle is attached to the grate can be varied; the components of the invention can be manufactured from other materials, as long as chemical compatibility is considered; and the number and size of sample-ports can be varied. The shape of the sample-ports can vary somewhat, but the rounded leading edge and square side and back edges are important to the predictable capture efficiency, and thus to the ability to sample representative runoff volumes of desired magnitudes.

We claim:

1. A runoff water monitoring system for sampling sheet-flow from a generally flat surface having an edge and an elongated recess contiguous to said edge and depending below said generally flat surface, said recess being elongated in a direction transverse to direction of sheet-flow, comprising:

an insert in said recess, said insert having an upper end, a grate member having a downwardly depending sample receptacle attachment sleeve and a grate plate, said grate plate having a predetermined number of sheet-flow metering apertures therein, a sample receptacle having an open end, and securement means for securing the open end of said sample receptacle on said attachment sleeve to receive water flowing through said sheet-flow metering apertures.

2. The runoff water monitoring system defined in claim 1 wherein said sheet-flow metering apertures are rectangular and have a leading or upstream edge and side and back edges and said leading edge is rounded.

3. The runoff water monitoring system defined in claim 2 wherein said side and back edges are square.

4. The runoff water monitoring system defined in claim 1 wherein said securement means includes groove means in said sleeve and an endless elastic member in said groove.

5. The runoff monitoring system defined in claim 1 wherein said sample receptacle attachment sleeve includes an internal baffle for trapping floating pollutants.

6. In a sheet-flow runoff water monitoring device, the improvement comprising:
   a metering grate member having a plurality of spaced sheet-flow metering apertures thereon, each sheet-flow metering aperture having a leading edge, side and back edges, said leading edge being shaped to enhance the capture of runoff water through said sheet-flow metering apertures, and a sample receptacle having an open end adapted to receive and collect all water flowing through said sheet-flow metering apertures.

7. The sheet-flow monitoring device defined in claim 6 wherein said sheet-flow monitoring apertures are rectangular and greater than at least ⅛ inch wide in the direction of sheet-flow.

8. The sheet-flow monitoring device defined in claim 6 wherein said leading edge is rounded and said side and back edges of said monitoring apertures are sharp-edged.

9. A collection receptacle for a runoff water monitoring system wherein metered runoff water is collected for analysis, said collection receptacle being flexible plastic and having a pair of side walls sealed to each other, an open top, and a tongue and groove press seal between said pair of side walls and located a predetermined distance below said open top.

10. The collection receptacle for runoff water as defined in claim 9 wherein said predetermined distance is about 50 mm.

11. A passive, simple to operate sheet-flow water quality monitoring device that can be easily configured to capture desired runoff volumes that are representative of the entire water column and sample area, and captures sheet-flow at a rate independent of runoff depth, comprising:
   (a) a removable sheet-flow metering grate section having a predetermined number of sheet-flow metering apertures,
   (b) a removable, modular sample receptacle,
   (c) a permanently installed insert, and
   (d) an attachment device for attaching said modular sample receptacle to said sheet-flow metering grate section so that it can be easily removed.

12. The sheet-flow water quality monitoring device of claim 11 wherein said grate section is made of a chemical resistant material, selected from the group comprising high-density polyethylene, Teflon®, and stainless steel.

13. The sheet-flow water quality monitoring device of claim 11 wherein said sample-port(s) have a rounded leading edge and square side and back edges.

14. The sheet-flow water quality monitoring device of claim 11 wherein said sample receptacle is made of a chemically inert material, selected from high-density polyethylene, Teflon®, and glass.

15. The sheet-flow water quality monitoring device of claim 11 wherein said insert is made of a durable, rust-resistant metal, selected from aluminum and stainless steel.

16. A method of sampling sheet-flow water runoff of a roadway surface having an edge comprising
   providing an open-topped recess contiguous to said edge of said roadway surface,
   closing off said open-topped recess with a metering grate having a plurality of spaced apart metering openings having rounded leading edges to enhance the capture of said sheet-flow runoff, and
   collecting all of the water passing over said rounded leading edges and through said metering openings.

17. A runoff water monitoring system for sampling sheet-flow from a generally flat surface having an edge and a recess contiguous to said edge and depending below said generally flat surface comprising a grate having a predetermined number of sheet-flow metering apertures therein, each of said sheet-flow metering apertures having a leading edge, said leading edge being shaped to enhance the capture of runoff water through said metering aperture, and a sample collection receptacle mounted in said recess and below said grate to receive water flowing through the sheet-flow metering apertures.

18. The runoff water monitoring system defined in claim 17 wherein said leading edge is rounded.

19. The runoff water monitoring system defined in claim 18 wherein the rounded leading edge has a radius of curvature of about 13 mm.

20. The runoff water monitoring system defined in claim 17 wherein said leading edge is beveled.

21. The runoff water monitoring system defined in claim 17 wherein said sheet-flow metering apertures are aligned in a row transverse to the direction of flow of said runoff water.

22. The runoff water monitoring system defined in claim 1 wherein said metering apertures have leading edges and said leading edges are shaped to enhance the capture of runoff water through said apertures.

23. The runoff water monitoring system defined in claim 22 wherein said leading edges are rounded.

24. The runoff water monitoring system defined in claim 22 wherein said leading edges are beveled.

* * * * *